United States Patent [19]

Herskowitz

[11] Patent Number: 5,681,284

[45] Date of Patent: Oct. 28, 1997

[54] INFUSION PUMP WITH TUBE SPIKE HOLDER

[76] Inventor: Glenn Herskowitz, 220 Hawthorne Ave., Larkspur, Calif. 94939

[21] Appl. No.: 491,498

[22] Filed: Jun. 16, 1995

Related U.S. Application Data

[63] Continuation-in-part of Ser. No. 331,883, Oct. 31, 1994, Pat. No. 5,554,123.

[51] Int. Cl.⁶ .................................................. A61M 37/00
[52] U.S. Cl. .......................... 604/141; 604/65; 604/67; 604/153
[58] Field of Search ................... 604/65–67, 140–141, 604/153, 403, 411, 415

[56] References Cited

U.S. PATENT DOCUMENTS

| | | | |
|---|---|---|---|
| 4,741,837 | 5/1988 | Brown | 604/134 |
| 5,059,182 | 10/1991 | Laing | 604/142 |
| 5,106,374 | 4/1992 | Apperson | 604/140 |
| 5,163,909 | 11/1992 | Stewart | 604/140 |
| 5,207,645 | 5/1993 | Ross | 604/141 |
| 5,308,335 | 5/1994 | Ross . | |
| 5,330,431 | 7/1994 | Herskowitz | 604/153 |
| 5,334,180 | 8/1994 | Adolf et al. | 604/411 |
| 5,348,539 | 9/1994 | Herskowitz | 604/141 |
| 5,399,166 | 3/1995 | Laing | 604/146 |
| 5,423,759 | 6/1995 | Campbell | 604/153 |
| 5,431,634 | 7/1995 | Brown | 604/153 |
| 5,433,704 | 7/1995 | Ross et al. | 604/141 X |
| 5,509,901 | 4/1996 | Milijasevic | 604/153 |

*Primary Examiner*—Sam Rimell
*Assistant Examiner*—Robert V. Racunas
*Attorney, Agent, or Firm*—Flehr Hohbach Test Albritton & Herbert LLP

[57] ABSTRACT

An infusion pump for infusing solutions from IV bags through tubing to patients. The pump comprises a housing having a compartment which receives an IV bag in a solution-dispensing position. The bag is placed over a bladder within the compartment, and the bladder is expanded by a pressurized fluid to apply a pushing force against the bag which collapses to infuse solution through the tubing. A pump in the housing pumps a fluid such as air into the bladder under influence of a control circuit. A pressure sensor indirectly senses pressure of fluid in the bladder through a pressure of pad which contacts the bladder wall. A control circuit generates a pressure signal responsive to movement of the pressure pad for operating a valve which directs fluid between the pump and bladder. A dispensing spike is provided for interconnecting a dispensing port of the bag in fluid communication with the tubing. The spike is formed with an annulus which cooperates with a wall of the housing to prevent unintended withdrawal of the spike from a dispensing port while infusion takes place. The annulus also operates a switch which is connected in the control circuit to ensure that infusion proceeds only when the bag is in its proper solution-dispensing position in the housing.

23 Claims, 6 Drawing Sheets

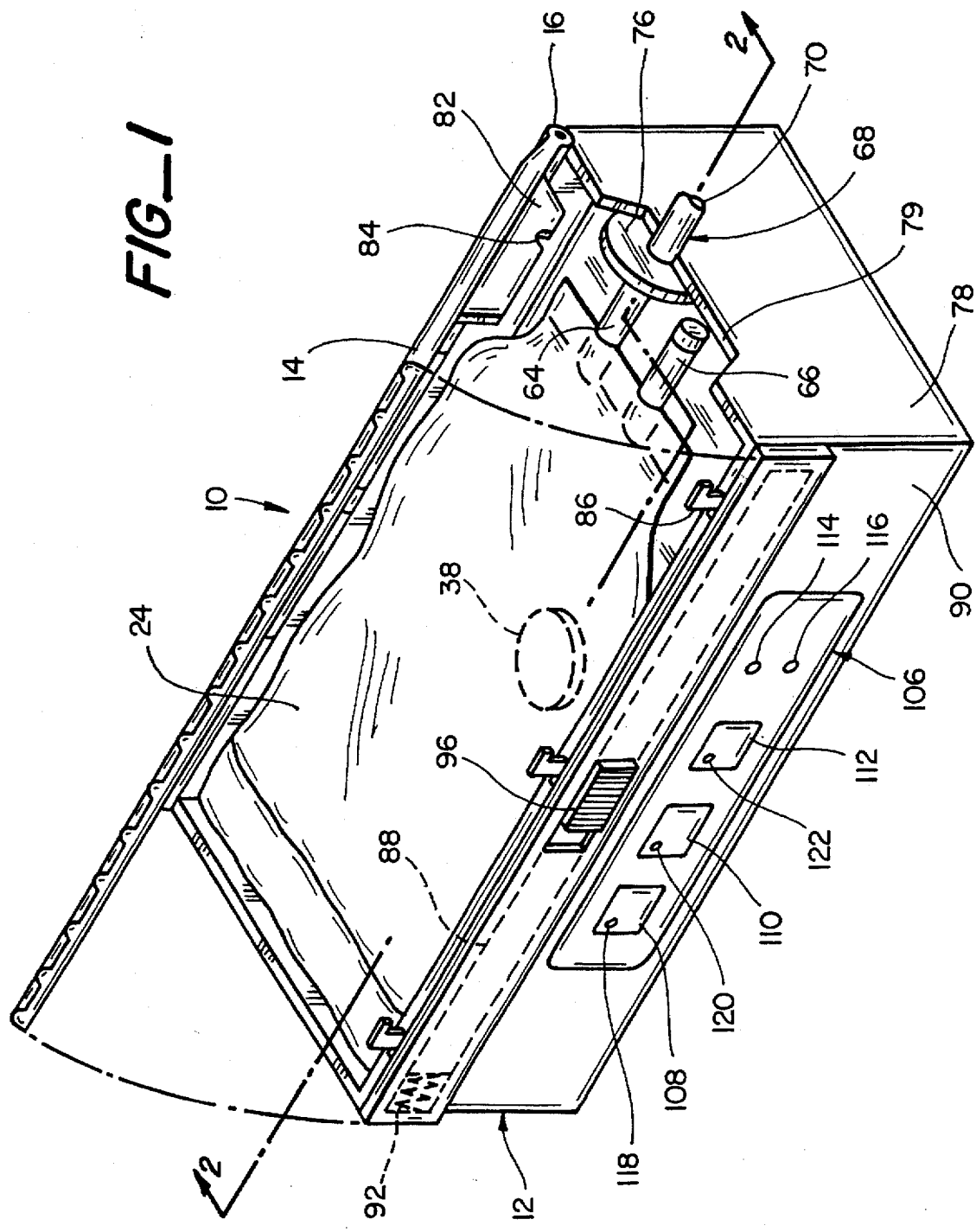
FIG_1

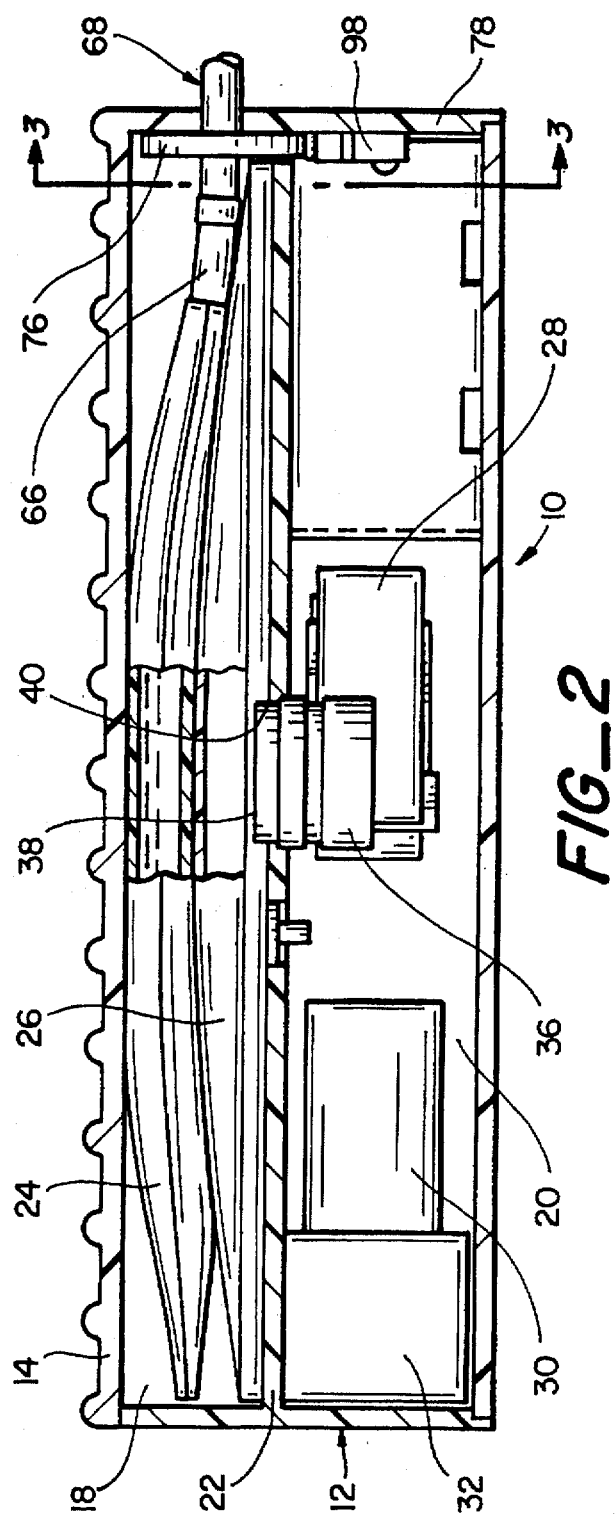
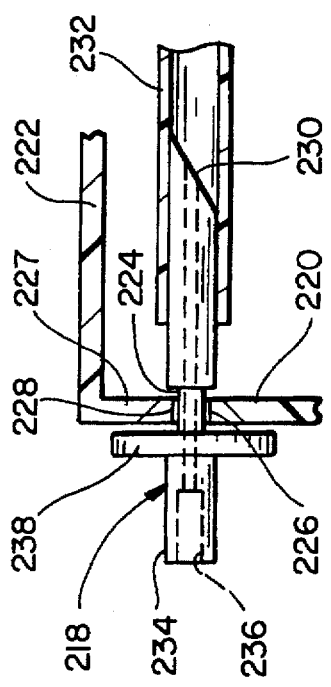
FIG_2
FIG_7

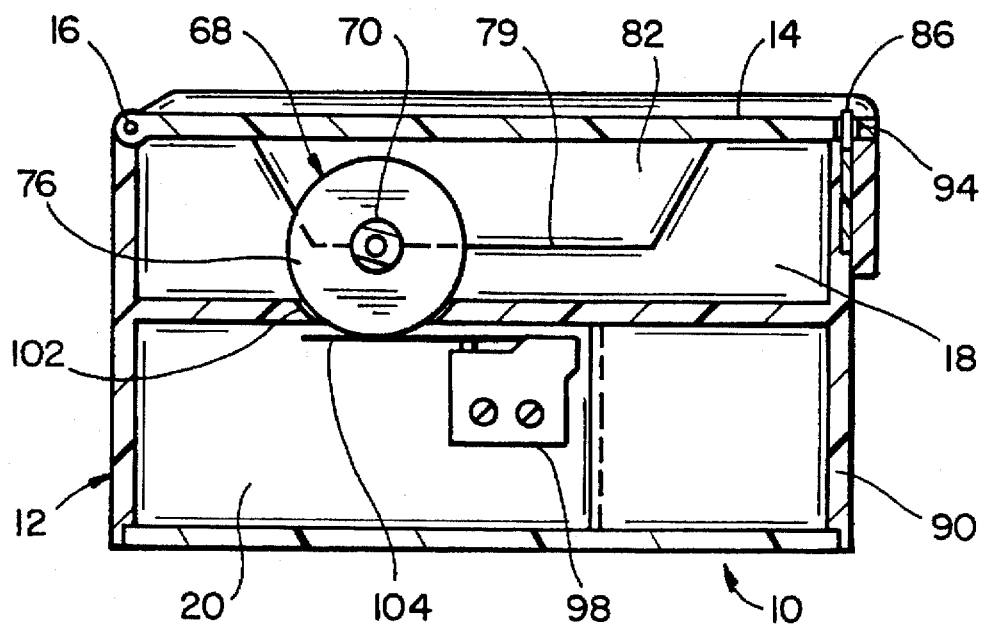
FIG_3
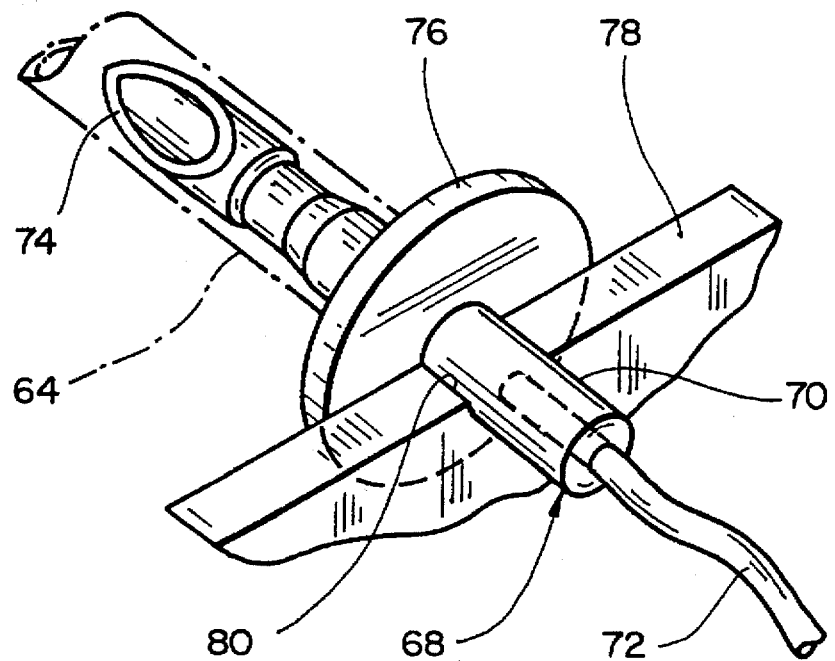
FIG_4

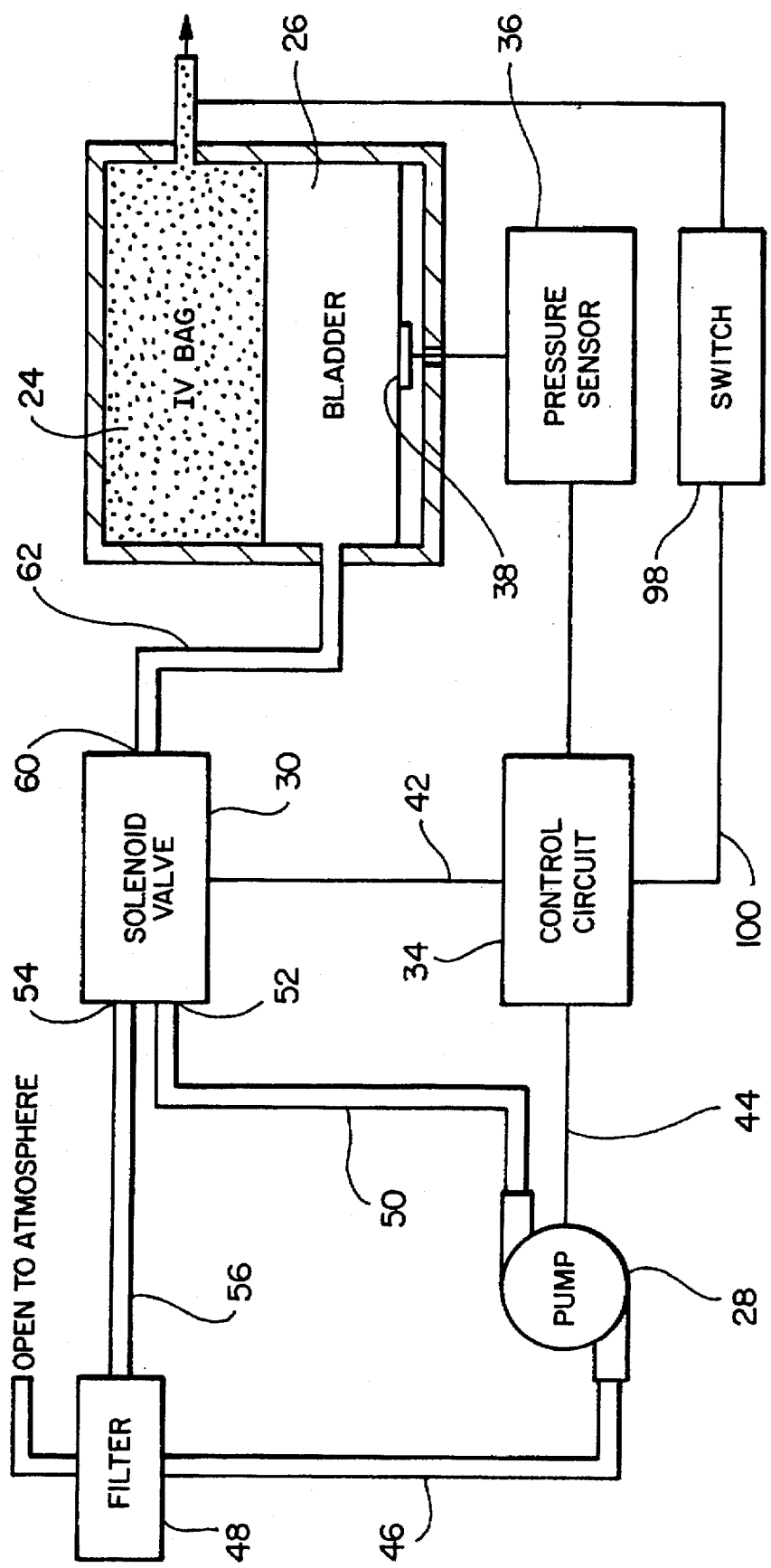

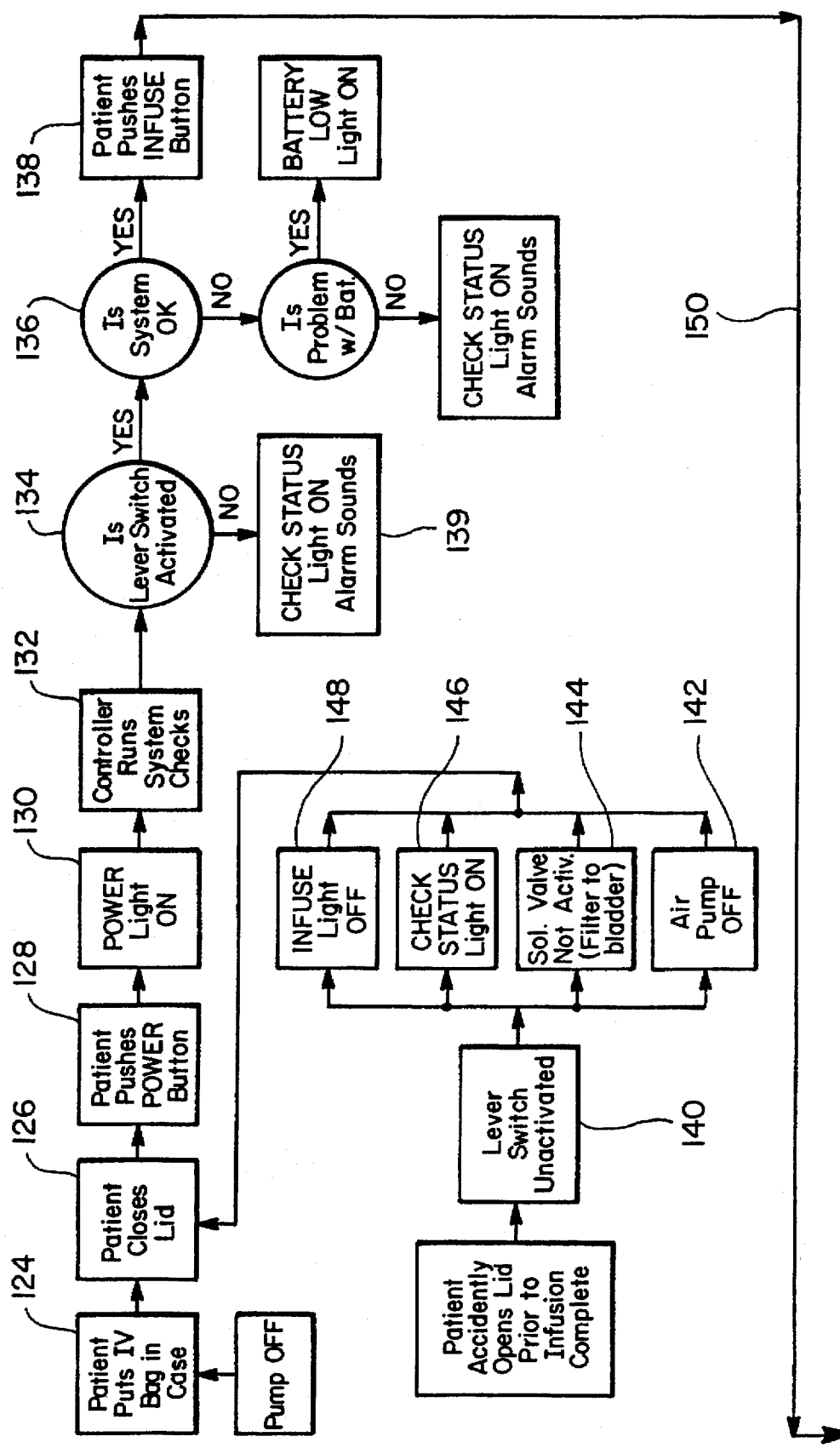
FIG_6A

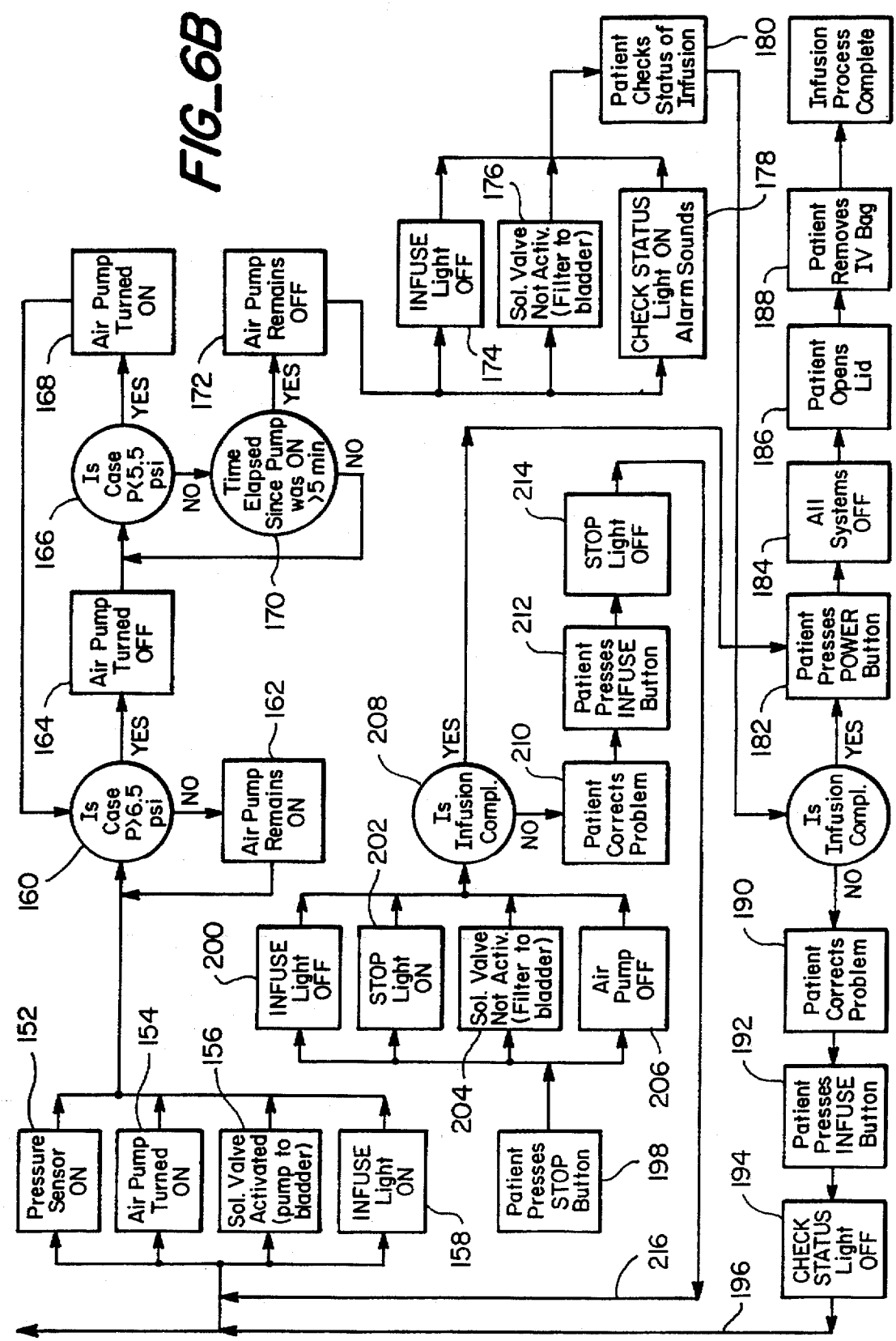

INFUSION PUMP WITH TUBE SPIKE HOLDER

This is a continuation-in-part of patent application Ser. No. 08/331,883, filed Oct. 31, 1994 and issued as U.S. Pat. No. 5,554,123 on Sep. 10, 1996.

BACKGROUND OF THE INVENTION

1. Field of the Invention

This invention relates in general to the infusion of intravenous (IV) solutions. In particular, the invention relates to portable IV infusion pumps for use by ambulatory and other patients.

2. Description of the Related Art

Infusion pumps are used to deliver various types of solutions intravenously to patients. A variety of drugs are commonly administered to patients by means of the intravenous solutions. Among the types of therapies requiring this kind of administration are chemotherapy, antibiotic therapy and antiviral therapy. In many cases, patients receive multiple daily therapies. Certain medical conditions require infusion of drugs in solution over relatively short periods of time, such as from 30 minutes to 2 hours. Infusion pumps have been developed in the prior art in an effort to meet these needs. There has been a requirement of providing portable infusion pumps for use by ambulatory patients and the like.

The different types of infusion pumps in the prior art include elastomeric pumps which squeeze the solution from flexible containers, such as balloons, into IV tubing for delivery to the patient. Spring-loaded pumps have also been provided to pressurize the solution containers or reservoirs. In certain infusion pump designs, cartridges containing flexible compound compartments that are squeezed by pressure rollers for discharging the solutions are provided, such as in U.S. Pat. No. 4,741,736. U.S. Pat. No. 5,330,431, issued to the inventor of the present invention, shows an infusion pump in which standard prefilled single dosage IV bags are squeezed by the use of a roller. U.S. Pat. No. 5,348,539, also issued to the inventor of the present invention, shows an infusion pump in which prepackaged IV bags are squeezed by a bladder which is actuated by a fluid pump from a reservoir.

Dispensing spikes have been provided for interconnecting IV tubing with the IV bags. The spikes penetrate through dispensing ports in the bags to permit the fluid to infuse through the tubing to the patient. U.S. Pat. 5,106,374 to Apperson discloses a spike having a locating flange which assists in locating the spike within the housing of an ambulatory infusion device.

The prior art infusion devices include arrangements for sensing the pressure of the IV bags to control the infusion procedure, such as for shutting off the infusion flow.

The need has been recognized for a portable infusion pump which controls the infusion process by indirectly sensing IV solution pressure without intrusion into the bag itself. It would also be desirable to provide such an infusion pump which provides a safe and reliable arrangement for sensing when the IV bag is in its proper solution-dispensing position within the compartment of the pump housing and which also ensures that the dispensing spike cannot be accidentally withdrawn from the bag's dispensing port when the infusion is in progress.

The need has been recognized for an infusion pump which obviates the foregoing and other limitations and disadvantages of prior art infusion pumps. Despite the various infusion pumps in the prior art, there has heretofore not been provided a suitable and attractive solution to these problems.

OBJECTS AND SUMMARY OF THE INVENTION

It is a general object of the present invention to provide a new and improved infusion pump for dispensing IV solutions to patients.

Another object is to provide an infusion pump of the type described which is of relatively small size and is inexpensive and simple to operate.

Another object is to provide an infusion pump of the type described which ensures against accidental separation of the dispensing spike from the dispensing port of the IV bag during the infusion procedure.

Another object is to provide an infusion pump of the type described which ensures that the IV bag is properly in its solution-dispensing position during the infusion procedure.

The invention in summary provides an infusion pump having a housing which provides a compartment for receiving an IV bag in a solution-dispensing position. A bladder mounted in the housing has a flexible wall which expands and contracts under influence of pressurized fluid from a pump. The bladder expands against the IV bag so that the solution is infused out of the bag through a dispensing port into IV tubing to the patient. This provides the operating means for collapsing the bag. Fluid pressure in the bladder is indirectly sensed by a non-intrusive sensor which is connected in a circuit that controls the pump. A dispensing spike interconnects the IV tubing with the dispensing port in the bag, and the spike has a structure which actuates a switch for enabling the control system when the bag is in its proper solution-dispensing position. When the lid of the housing is closed, the spike is captured and held in place to prevent against unintended withdrawal during the infusion procedure.

The foregoing and additional objects and features of the invention will appear from the following specification in which the several embodiments have been set forth in detail in conjunction with the accompanying drawings.

BRIEF DESCRIPTION OF THE DRAWINGS

FIG. 1 is a perspective view illustrating an infusion pump in accordance with one embodiment of the invention.

FIG. 2 is an axial section view to an enlarged scale taken along the line 2—2 of FIG. 1.

FIG. 3 is a cross-sectional view taken along line 3—3 of FIG. 2.

FIG. 4 is a fragmentary perspective view to an enlarged scale showing components of the dispensing spike seated in the wall of the housing of the infusion pump shown in FIGS. 1 and 2.

FIG. 5 is a schematic diagram of the control system for the infusion pump shown in FIGS. 1 and 2.

FIGS. 6A and 6B comprise a flow chart showing the method steps in the operation of the infusion pump of the invention.

FIG. 7 is a fragmentary sectional view of another embodiment showing details of an arrangement for capturing the dispensing spike.

DESCRIPTION OF THE PREFERRED EMBODIMENTS

In the drawings, FIGS. 1 and 2 illustrate generally at 10 a portable infusion pump according to a preferred embodiment of the invention. Infusion pump 10 provides an ambulatory system which enables health care professionals to infuse patients directly from single dose container bags which are pre-filled with IV solutions. Infusion pump 10 of the invention is suitable for use in homes, hospitals or clinics. It is also readily adapted for operation in any position, such as resting on a table with the patient in bed, or it could be carried by the patient.

Infusion pump 10 is comprised of a box-shaped housing 12 having a lid 14 which pivots open and closed about a hinge 16. The interior of the housing is divided into an upper compartment 18 and lower compartment 20 by a horizontal flat plate 22. The upper compartment is sized and shaped commensurate with the size and shape of a standard large (115 cc) IV bag 24, and the compartment can also contain a standard small (50 cc) IV bag.

An inflatable bladder 26 is mounted across the upper surface of plate 22 within the upper compartment. The opposite walls of the bladder are hermetically sealed together about their periphery to provide a closed internal volume for containing a fluid under pressure. In the present embodiment, the fluid is a gas, preferably air, although liquid fluids could also be employed, such as a low viscosity, non-toxic oil.

Lower compartment 20 of the housing mounts an air pump 28, a two-position solenoid valve 30, a battery compartment 32 and a printed circuit board, not shown, which contains components of the electric control circuit 34 shown schematically in FIG. 5. A pressure sensor 36 is mounted from plate 22 and depends downwardly into the lower compartment. The pressure sensor includes a moveable pressure pad 38 which extends upwardly through a central opening 40 in plate 22 into juxtaposed relationship with the lower wall of bladder 26. Expansion and contraction of the bladder as its internal fluid pressure increases and decreases correspondingly causes up and down movement of the pressure pad. The pressure sensor generates an electric pressure signal responsive to movement of the pressure pad, and this signal is directed through line 42 into control circuit 34. The control circuit is powered by suitable dry cells, not shown, mounted in the battery compartment.

Control circuit 34 is also connected through line 44 to operate the air pump. The pump inlet draws atmospheric air through inlet tube 46 and filter 48, with pressurized air being directed out through tube 50 into the solenoid valve 30. This valve has a normally closed inlet 52 connected with air pump 28, and a normally open outlet 54 is connected via tube 56 through filter 48 and tube 58 to atmosphere. An outlet 60 leads through tube 62 to the bladder. In the normally open position of the valve, the inner volume of the bladder is opened through outlet 54 to atmospheric air so that the IV bag cannot be pressurized. At the same time, inlet 52 blocks out pressurized air from the pump. When the control circuit sends a signal through the line 42 to the valve, inlet 52 is opened so that the valve directs pressurized air from the pump into the bladder while outlet 54 is closed.

With lid 14 in its open position shown in FIG. 1, IV bag 24 is inserted so that it lies flat across the upper wall of the bladder. In this solution-dispensing position of the bag, the bag's dispensing port 64 and filling port 66 extend toward the right of the compartment, as viewed in FIGS. 1 and 2.

FIG. 4 illustrates dispensing spike 68 in accordance with the invention which provides means for releasably interconnecting the IV tubing with the IV bag. Dispensing spike 68 is comprised of a tubular body 70 having a proximal end adapted for receiving the end of IV tubing 72. The distal end of the tubular body is formed into a piercing spike 74 which is adapted to pierce through the closed end of dispensing port 64. This opens the inner channel of the spike to solution within the bag. The dispensing spike thereby interconnects the end of the IV tubing in fluid communication with the solution in the bag.

Dispensing spike 68 includes an annulus 76 formed about the tubular body. The annulus has a diameter which is sufficiently large to enable the hand of the user to apply a force along the longitudinal axis of the body for inserting and removing the spike into and from the dispensing port. A diameter in the range of 0.6 " to 1.0 ", and preferably 0.8 ", is suitable for this purpose.

It is another important feature of the invention that annulus 76, in cooperation with housing end wall 78 and lid 14, is releasably captured and securely held in place when the bag is in its proper solution-dispensing position. Toward this objective, a notch 79 (FIG. 3) is formed along the upper side of housing end wall 78. A U-shaped groove 80 is formed in the notch at a position for seating about the lower portion of tubular body, as best shown in FIG. 4. In this position, annulus 76 fits within the upper compartment with its outer surface seated against the housing end wall. Outward forces on the tubular body, such as when the IV tubing is pulled, are resisted by the annulus which thereby holds the spike against displacement from the IV bag as long as the lid is closed. The corresponding end of the lid is formed with a downwardly projecting ridge 82 which matches the shape of the notch. U-shaped groove 84 (FIG. 1) is formed in the lower side of the ridge, and this groove seats against the upper portion of tubular body 70 when the lid is closed.

Lid 14 is releasably held in its closed position by means of a plurality, shown as three, of latches 86 which are mounted at spaced positions on a slidebar 88. The slidebar is mounted for back and forth movement across the upper edge of housing front wall 90. A spring 92 is mounted at one end of the slidebar to urge it toward the right, as viewed in FIG. 1. With the slidebar urged to the right, the latches engage lid notches 94 (FIG. 3) to hold the lid down. A manually operated latch release button 96 carried on the slidebar projects through an opening in the front of the housing to permit the user to move the slidebar to the left so that the latches release from the lid.

Another important feature of the invention is the provision of an on-off switch 98 which, in combination with dispensing spike annulus 76, generates a bag-in-place signal when the bag is in its proper solution-dispensing position. The bag-in-place signal is directed through line 100 into the control circuit for controlling the infusion procedure. The end of horizontal plate 22 is formed with a slot 102 (FIG. 3) through which spike annulus 76 projects downwardly into the lower compartment. Switch 98 is provided with an actuating arm 104, and the switch is positioned in the lower compartment so that the arm projects into an interference relationship with the portion of annulus which extends downwardly through slot 102. When the dispensing spike is out of the position shown in FIG. 1, such as when the IV bag is either out of the compartment or improperly positioned, then annulus 76 cannot fit fully down through the slot. This permits the actuating arm to move upwardly so that switch 98 is operated to a position in which the bag-in-place signal is disabled.

While an air filter 48 is shown for filtering air from the atmosphere into pump 28, the invention contemplates that the filter could be eliminated with the pump drawing inlet air directly from the atmosphere, and with exhaust air from the bladder being sent through outlet 54 directly to atmosphere.

The invention also contemplates an arrangement in which the outlet from pump 28 directs air through a line leading directly into bladder 26. In such an arrangement, the solenoid valve 30 would have one inlet connected with the bladder and one outlet which directs air to the atmosphere either directly or through an air filter. The valve would be operated by a control circuit of the type shown in FIG. 5 between one position in which the valve inlet is closed while the pump fills the bladder with pressurized air, and in another position in which the valve inlet is opened so that pressurized air from the bladder is discharged through the valve to atmosphere.

Housing 12 includes a control panel 106 having a power-on pushbutton 108, an infuse pushbutton 112. The pushbutton 112. The panel also includes a light 114 providing a battery low condition signal, and a light 116 providing a check status signal. Pushbutton 108 is provided with a light 118 for indicating a power-on condition, pushbutton 110 is provided with a light 120 indicating an infuse condition, and pushbutton 112 is provided with a light 122 for indicating a stop condition.

The flow chart comprised of FIGS. 6A and 6B illustrates the steps in the method of operation of diffusion pump 10. With air pump 28 turned off, the IV bag is placed into its solution-dispensing position within the upper compartment of the housing at step 124. The lid is then closed at step 126, which is followed by the patient, or health care professional, pushing the power button at step 128. This turns on the power light at step 130, and the control circuit runs its system checks at step 132. If the spike annulus properly actuates switch 98 at light step 134, a "yes" indication is directed into the "system okay" logic step 136. If not, the check status light is turned on and an automatic alarm sounds at step 139. If the "system okay" condition exists, the infuse button is pushed at step 138. If the lid is accidentally opened prior to completion of infusion, switch 98 is deactivated at step 140. The control circuit responds and turns the air pump off at step 142, valve 30 is deactivated at step 144 so that air is exhausted from the bladder through the filter to atmosphere, the check status light is turned on at step 146, and the infuse light is turned off at step 148.

The signal generated from the infuse button being turned on is directed into line 150 which: turns on pressure sensor 36 at step 152, turns the air pump on at step 154, activates valve 30 at step 156 which directs pressurized air from the pump into the bladder, and turns the infuse light on at step 158. Next, the logic checks whether the pressure sensor senses a bladder pressure of a greater than a predetermined level, for example greater than 6.5 psi, at step 160. If that level or above is not sensed, then the air pump remains on at step 162. When the bladder pressure reaches or exceeds that level, then the air pump is turned off at step 164. The circuit logic next determines at step 166 whether the bladder pressure is below a lower predetermined level, for example 5.5 psi. If it is below that level, then the air pump is turned on at step 168. If not, then the logic at step 170 determines if the time elapsed since the pump was on is greater than 5 minutes. If so, then the air pump remains off at step 172. Next, the infuse light is turned off at step 174, valve 30 is deactivated to exhaust air from the bladder at step 176, the check status light is on and the alarm sounds at step 178.

The method then proceeds to step 180 where the patient or health care professional checks the status of infusion. If the infusion is complete, the power button is turned off at step 182. This turns all systems off at step 184 so that the patient can open the lid at step 186, and remove the IV bag at step 188. If the infusion is not complete, then the patient can correct the problem at step 190 and press the infuse button at step 192. This turns the check status light off at step 194, and the logic proceeds through line 196 to repeat the infusion process.

If at any time during the infusion process the patient presses the stop button at step 198, then the infuse light is turned off at step 200, the stop light is turned on at step 202, the solenoid valve is deactivated at step 204 and the air pump is turned off at step 206. The logic then determines at step 208 if infusion is complete. If so, the logic proceeds to step 182 so that the power button can be turned off. If the infusion is not complete, then the patient can correct the problem at step 210 and then press the infuse button at step 212 which turns the stop light 122 off at step 214. The logic then proceeds through line 216 to repeat the infusion procedure.

FIG. 7 illustrates another embodiment providing a modified dispensing spike 218 for releasably holding the spike in a pump housing 220 when a lid 222 is closed. Dispensing spike 218 is formed about its proximal end with an annular groove 224. The annular recess portion within the groove releasably fits on its lower side into a matching U-shaped seat 226 which is formed on the upper edge of the housing end wall. The lid has a downward protecting portion 227 at its front end which is formed with a similar U-shaped seat 228 which moves into register with and fits into the top side of the spike groove when the lid is closed. The sharpened end 230 of the spike penetrates into the IV bag dispensing port 232. A tubular body 234 of the spike is formed with an internal bore 236 which receives the end of the IV tubing, not shown. An annulus 238 formed about the body provides a push surface against which force can be applied by the user's hand to insert and remove the spike into and from the dispensing port. With the lid closed, the upper and lower seats 226 and 228 fit about the spike groove so that the spike is locked against unintended removal from the housing during the infusion process.

While the foregoing embodiments are presently considered to be preferred, it is understood that numerous variations and modifications may be made therein by those skilled in the art and it is intended to cover in the appended claims all such variations and modifications as fall within the true spirit and scope of the invention.

What is claimed is:

1. An infusion pump for infusing intravenous solution from a bag through intravenous tubing into a patient, the bag having a flexible sidewall which at least partially encloses an interior chamber to contain the solution, the bag further having a dispensing port for releasable connection with an end of the tubing, the infusion pump comprising the combination of: a housing having a compartment for removably receiving and supporting the bag in a solution-dispensing position; a bladder having a flexible wall which moves by expansion and contraction responsive to respective increase and decrease in the pressure of a fluid within the bladder; means for mounting the bladder within the housing in a position for applying a pushing force against the sidewall of the bag to collapse the bag responsive to expansion of the bladder wall whereby solution within the chamber in the bag is infused out through the dispensing port; pump means for pumping fluid into the bladder to increase said pressure in an effective amount to cause said collapse of the bag; pressure sensor means for generating an electrical signal representing fluid pressure responsive to said expansion and contraction movement of the bladder wall for indirectly sensing said pressure of the fluid within the bladder; and control means for controlling the pump means between a fluid pumping mode and an off mode responsive to said electrical signal.

2. An infusion pump as in claim 1 in which: said pressure sensor means comprises a pressure pad positioned in juxtaposed relationship with a portion of the bladder wall and moveable therewith for generating said electrical signal.

3. An infusion pump as in claim 2 in which: said pump means comprises a fluid pump for directing fluid under electrical along an inlet path into the bladder; and said control means comprises valve means for closing off fluid flow along the inlet path responsive to said pressure signal being at a predetermined magnitude.

4. An infusion pump as in claim 3 in which: said fluid pump comprises and air pump and said fluid is air.

5. An infusion pump for infusing intravenous solution from a bag through intravenous tubing into a patient, the bag having a flexible sidewall which at least partially encloses an interior chamber to contain the solution, the bag further having a dispensing port for releasable connection with an end of the tubing, the infusion pump comprising the combination of: a housing having a compartment for removably receiving and supporting the bag in a solution-dispensing position; a bladder having a flexible wall which moves by expansion and contraction responsive to respective increase and decrease in the pressure of a fluid within the bladder; means for mounting the bladder within the housing in a position for applying a pushing force against the sidewall of the bag to collapse the bag responsive to expansion of the bladder wall whereby solution within the chamber in the bag is infused out through the dispensing port; pump means for pumping fluid into the bladder to increase said pressure in an effective amount to cause said collapse of the bag; pressure sensor means for generating a fluid pressure signal responsive to said expansion and contraction movement of the bladder wall for indirectly sensing said pressure of the fluid within the bladder; and control means for controlling the pump means between a fluid pumping mode and an off mode responsive to said fluid signal, said control means comprises signal means for generating a bag-in-place signal when the bag is in said solution-dispensing position, said control means controlling the pump means to the fluid pumping mode only responsive to the bag-in-place signal.

6. An infusion pump as in claim 5 in which said signal means comprises a switch carried by the housing and operable between on and off conditions together with interconnect means for releasable interconnecting said end of the tubing in fluid communication with said chamber in the bag, said interconnect means comprising a spike for connecting into the dispensing port and a switch-operating structure which is in a position to actuate the switch to its on condition responsive to the bag being in said solution-dispensing position when the spike is connected into the dispensing port.

7. An infusion pump as in claim 6 in which the interconnect means further comprises a tubular body which carries the spike and said switch-operating structure comprises an annulus mounted about the tubular body.

8. An infusion pump as in claim 7 in which the annulus has a diameter sufficiently large for enabling the hand of a user to apply a force along the longitudinal axis of the tubular body for inserting and removing the spike into and from the dispensing port.

9. An infusion pump as in claim 7 in which the housing includes capture means for releasably capturing and holding the tubular body from displacement relative to the housing when the bag is in the solution-dispensing position and the spike is connected into the dispensing port whereby the spike is restrained from unintended withdrawal from the dispensing port.

10. An infusion pump as in claim 9 in which the capture means comprises a wall in the housing having a seat for holding the tubular body in a position where the annulus is juxtaposed with a portion of the wall within the housing, said wall restraining the annulus to prevent movement of the tubular body out of the seat.

11. An infusion pump for infusing intravenous solution from a bag through intravenous tubing into a patient, the bag having a flexible sidewall which at least partially encloses a chamber to contain the solution, the bag further having a dispensing port for releasable connection with an end of the tubing, the infusion pump comprising the combination of: a housing having a compartment for removably receiving and supporting the bag in a solution-dispensing position; operating means for applying a force against the sidewall of the bag to collapse the bag and infuse solution within the chamber out through the dispensing port; interconnect means for releasably interconnecting said end of the tubing in fluid connection with said chamber in the bag, said interconnect means comprising a dispensing spike, means for releasably connecting the spike with said end of the tubing, said dispensing spike having an annular groove together with an outlet end positioned distally of the groove for connection with said dispensing port of the bag; said housing having a structure positioned in register with said annular groove when the outlet end of the spike is connected with the dispensing port; and means for moving said structure into and out of lockable relationship with said annular groove.

12. An infusion pump as in claim 11 in which said means for moving the structure comprises a lid mounted on the housing for movement between open and closed positions for enabling respective insertion and removal of the bag into and from said compartment, and groove-engaging means on the lid for engaging the annular groove and preventing displacement of the dispensing spike relative to the bag when the structure is in register with the spike and the lid is in its closed position.

13. An infusion pump for infusing intravenous solution from a bag through intravenous tubing into a patient, the bag having a flexible sidewall which at least partially encloses a chamber to contain the solution, the bag further having a dispensing port for releasable connection with an end of the tubing, the infusion pump comprising the combination of: a housing having a compartment for removably receiving and supporting the bag in a solution-dispensing position; operating means for applying a force against the sidewall of the bag to collapse the bag and infuse solution within the chamber out through the dispensing port; interconnect means for releasable interconnecting said end of the tubing in fluid communication with said chamber in the bag, said interconnect means comprising a dispensing spike, said dispensing spike having means for releasably connecting the spike with said end of the tubing, said dispensing spike when connected with the end of the tubing being in a set position relative to the housing when the bag is in its solution-dispensing position; and control means for enabling said operating means to apply said force responsive to the dispensing spike being in its set position.

14. An infusion pump as in claim 13 in which: the dispensing spike has a tubular body; and the housing includes capture means for releasably capturing and holding the tubular body against displacement with respect to the housing when the bag is in the solution-dispensing position and the dispensing spike is connected into the dispensing port.

15. An infusion pump as in claim 14 which includes: an annulus carried by the tubular body; and the capture means comprises a wall in the housing having a seat for holding the tubular body in a position where the annulus is juxtaposed with a portion of the wall within the housing, said wall restraining the annulus in the seat for preventing unintended movement of the dispensing spike out of the dispensing port.

16. An infusion pump as in claim 13 in which: the dispensing spike has a tubular body and a part carried on the tubular body, the part having a size sufficiently large for enabling the hand of a user to apply a force along the longitudinal axis of the tubular body for inserting and removing the spike into and from the dispensing port.

17. An infusion pump for infusing intravenous solution from a bag through intravenous tubing into a patient, the bag having a flexible sidewall which at least partially encloses a chamber to contain the solution, the bag further having a dispensing port for releasable connection with an end of the tubing, the infusion pump comprising the combination of: a housing having a compartment for removably receiving and supporting the bag in a solution-dispensing position; operating means for applying a force against the sidewall of the bag to collapse the bag and infuse solution within the chamber out through the dispensing port; interconnect means for releasable interconnecting said end of the tubing in fluid communication with said chamber in the bag, said interconnect means comprising a dispensing spike adapted for connection with said end of the tubing, said dispensing spike when connected with the end of the tubing being in a set position relative to the housing when the bag is in its solution-dispensing position; and control means for enabling said operating means to apply said force responsive to the dispensing spike being in its set position, said control means comprises signal means for generating a bag-in-place signal when the bag is in said solution-dispensing position, said control means enabling said operating means to apply said force only responsive to the bag-in-place signal.

18. An infusion pump as in claim 17 in which said signal means comprises a switch carried by the housing and operable between on and off conditions, and said dispensing spike further comprises a switch-operating structure which is in a position to actuate the switch to its on condition responsive to the bag being in said solution-dispensing position when the dispensing spike is connected into the dispensing port.

19. An infusion pump for infusing intravenous solution from a bag through tubing into a patient, the bag having a flexible sidewall which at least partially encloses an interior chamber to contain a solution, the bag further having a dispensing port, the infusion pump comprising the combination of: a housing having a compartment for removably receiving and supporting the bag in a solution-dispensing position, said housing having an opening of a predetermined size; a bladder having a flexible wall which moves by expansion and contraction responsive to respective increase and decrease in the pressure of a fluid within the bladder; said bladder being mounted in the housing so that said expansion of the flexible wall applies a pushing force against the sidewall of the bag to collapse the bag responsive to expansion of the bladder wall whereby solution within the chamber in the bag is infused out through the dispensing port; pump means for pumping fluid into the bladder to increase said pressure in an effective amount to cause such collapse of the bag; a spike which is sized for fitting within said opening in the housing, said spike including means for releasably connecting the spike with said tubing, a member carried by the spike, said member having a part which, when the spike is fitted within said opening, is positioned within the housing, said part being of a size greater than said predetermined size of the opening to prevent unintended withdrawal of the spike from the housing.

20. An infusion pump for infusing intravenous solution from a bag through tubing into a patient, the bag having a flexible sidewall which at least partially encloses an interior chamber to contain a solution, the bag further having a dispensing port, the infusion pump comprising the combination of: a housing having a compartment for removably receiving and supporting the bag in a solution-dispensing position, said housing having an opening of a predetermined size; a bladder having a flexible wall which moves by expansion and contraction responsive to respective increase and decrease in the pressure of a fluid within the bladder; said bladder being mounted in the housing so that said expansion of the flexible wall applies a pushing force against the sidewall of the bag to collapse the bag responsive to expansion of the bladder wall whereby solution within the chamber in the bag is infused out through the dispensing port; pump means for pumping fluid into the bladder to increase said pressure in an effective amount to cause such collapse of the bag; a spike which is sized for fitting within said opening in the housing, a member carried by the spike, said member having a part which, when the spike is fitted within said opening, is positioned within the housing, said part being of a size greater than said predetermined size of the opening to prevent unintended withdrawal of the spike from the housing, a switch carried by the housing and operable from an off mode to an on mode responsive to said port being in said position within the housing, and means for providing a bag-in-place signal responsive to said on mode of the switch.

21. An infusion pump as in claim 20 in which said spike includes means for interconnecting said tubing with the dispensing port for establishing fluid communication with said chamber in the bag.

22. An infusion pump as in claim 21 in which said means for interconnecting comprises a tubular body which carries the spike and said part comprises an annulus mounted about the tubular body.

23. An infusion pump as in claim 19 in which said opening comprises a seat in the housing which is sized for holding said member of the spike in a position where said part is juxtaposed with a portion of the seat within the housing, said seat restraining the part to prevent said unattended withdrawal of the spike from the housing.

* * * * *

UNITED STATES PATENT AND TRADEMARK OFFICE
CERTIFICATE OF CORRECTION

PATENT NO. : 5,681,284
DATED : October 28, 1997
INVENTOR(S) : GLENN HERSKOWITZ

It is certified that error appears in the above-indentified patent and that said Letters Patent is hereby corrected as shown below:

In Col. 7, line 7, delete "electrical" and substitute --pressure--; line 9, delete "pressure" and substitute --electrical--; and line 12, delete "and" (first occurrence) and substitute --an--.

In Col. 10, line 39, delete "port" and substitute --part--.

Signed and Sealed this

Tenth Day of February, 1998

Attest:

BRUCE LEHMAN

*Attesting Officer*  *Commissioner of Patents and Trademarks*